United States Patent [19]

Cheiky-Zelina

[11] Patent Number: 5,764,538
[45] Date of Patent: Jun. 9, 1998

[54] SYSTEM INTERFACE FOR MICROWAVE CONDUCTIVITY SENSOR

[75] Inventor: Margaret Ann Cheiky-Zelina, Cleveland, Ohio

[73] Assignee: Man-Gill Chemical Company, Cleveland, Ohio

[21] Appl. No.: 566,503

[22] Filed: Dec. 4, 1995

[51] Int. Cl.$^6$ ................................................ G01N 15/00
[52] U.S. Cl. .................................. 364/555; 324/636
[58] Field of Search ................................ 364/555, 636; 73/861.95, 204.23; 604/65

[56] References Cited

U.S. PATENT DOCUMENTS

| 4,689,553 | 8/1987 | Haddox | 324/58.5 |
| 5,025,222 | 6/1991 | Scott et al. | 324/639 |
| 5,260,665 | 11/1993 | Goldberg et al. | 324/636 |
| 5,334,941 | 8/1994 | King | 324/637 |
| 5,548,217 | 8/1996 | Gibson et al. | 324/316 |

OTHER PUBLICATIONS

Iotech Catalog, p. 65, Jan. 1995.
The Nist 60–Millimeter Diameter Cylindrical Cavity Resonator: Performance Evaluation for Permittivity Measurements, Eric J. Vanzura, Richard G. Geyer, and Michael D. Janezic, Aug. 1993, National Institute of Standards and Technology Technical Note.

*Primary Examiner*—Emanuel T. Voeltz
*Assistant Examiner*—Patrick Assouad
*Attorney, Agent, or Firm*—Renner, Otto, Boisselle & Sklar, P.L.L.

[57] ABSTRACT

A system interface for acquiring data from a microwave conductivity sensor which produces data related to an electrical property of a fluid within a resonant cavity included in the microwave conductivity sensor, the system interface including a memory storing a program; and a computer for executing the program stored in the memory for causing the computer to prompt the microwave conductivity sensor to transmit the data to the computer and to parse the data for particle size information.

20 Claims, 6 Drawing Sheets

SYSTEM INTERFACE FOR MICROWAVE CONDUCTIVITY SENSOR

TECHNICAL FIELD

The present invention relates generally, as is indicated, to a system interface for a microwave conductivity sensor (MCS). More particularly, the present invention relates to a computer based interface for obtaining and evaluating data from a MCS according to user defined intervals and alarm limits.

BACKGROUND OF THE INVENTION

Recently, a microwave conductivity sensor (MCS) has been developed for the purpose of detecting the presence of conductive particles in a resonant cavity. A fluid containing conductive particles is placed in the resonant cavity and the Q factor, amplitude and/or phase of the resonant signal within the resonant cavity is detected. The presence of conductive particles in the fluid affects the overall dielectric constant within the resonant cavity. Consequently, changes in the size of conductive particles within the fluid will result in a change in the Q factor, phase, and/or amplitude of the microwave signal within the resonant cavity. Furthermore, changes in the oxidation level within the fluid can similarly effect a change in the dielectric constant within the resonant cavity. By analyzing the Q factor, phase and/or amplitude of the microwave signal, information regarding the oxidation level of the fluid can also be obtained.

Figure 1:
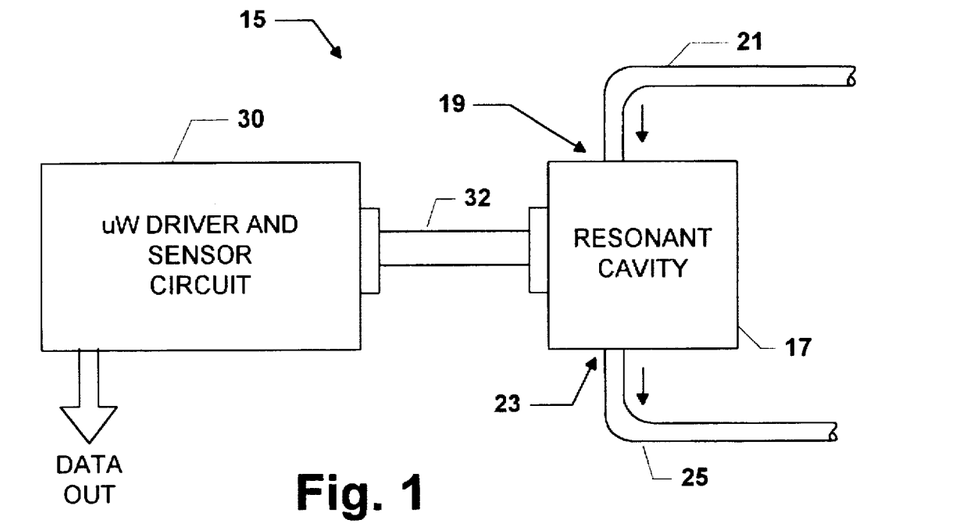
FIG. 1 is a block diagram of a microwave conductivity sensor (MCS) for use in accordance with the present invention.

FIG. 1 illustrates an exemplary MCS which is generally designated 15. The MCS 15 includes a resonant cavity 17 of suitable size and shape for sustaining resonance of a microwave signal therein. The resonant cavity 17 includes an input port 19 through which fluid from an input pipe 21 is pumped into the resonant cavity 17. In addition, the resonant cavity 17 includes an output port 23 out of which the fluid in the resonant cavity 17 flows by way of an output pipe 25. The flow rate of the fluid through the resonant cavity 17 is controlled such that the resonant cavity 17 preferably remains filled uniformly with the fluid as fluid continues to flow therethrough. The fluid itself can be a lubricating fluid or other type fluid whose conductive particle concentration and/or oxidation level may be of interest. For example, machine wear analysis often involves the study of the particulate found in the machine lubricating fluid. The MCS 15 is useful for analyzing these properties.

Connected to the resonant cavity is a microwave driver and sensor circuit 30. The circuit 30 includes, for example, a microwave source (not shown) for providing a microwave excitation signal to the resonant cavity 17 by way of bus 32. The resonant signal within the resonant cavity 17 is detected and is returned to the circuit 30 via the bus 32. The circuit 30 then processes the signal received from the resonant cavity to produce data representing the Q factor, phase, and/or amplitude of the resonant signal. As mentioned above, such data is indicative of the size of the conductive particles within the fluid. This data is then output to a data storage medium or the like for subsequent processing.

Figure 2:
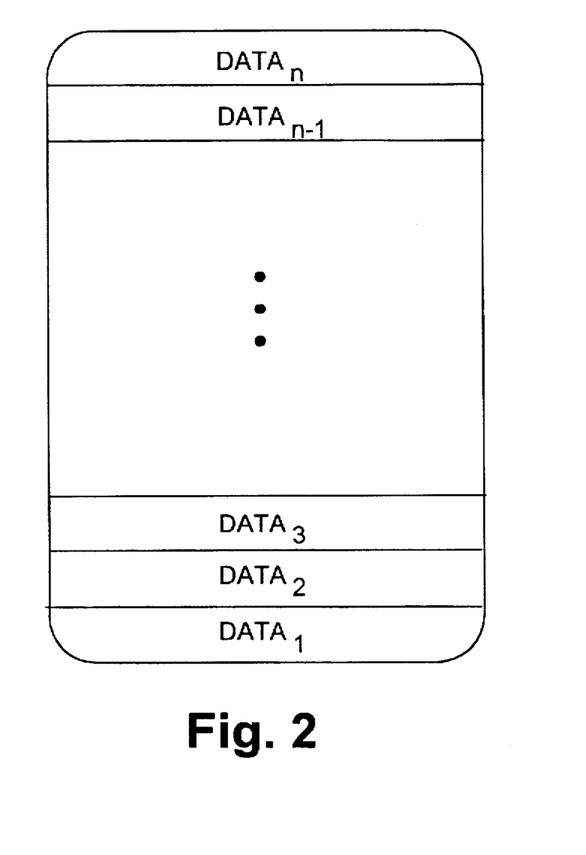
FIG. 2 is a schematic diagram representing raw data which is output by the MCS.

FIG. 2 represents the type of data which is periodically provided by the MCS 15. The data is output as a string of data samples $DATA_1, \ldots, DATA_n$, for example, in time ordered sequence based on the time at which the data samples where taken. In the exemplary embodiment, the sampled data is stored within the MCS 15 in a FIFO data buffer of size n. Provided the MCS 15 continuously samples the data, the data buffer stores the last n samples.

Despite the obvious utility of the MCS 15, there are some substantial drawbacks associated with the use of a sensor. For example, the MCS 15 can produce voluminous amounts of raw data indicating the Q factor, phase, and/or amplitude measured over time. Such raw data is useful for performing trending analyses particularly for purposes of evaluating machine wear. However, the vast amounts of raw data accumulated over time will quickly fill up a storage medium such as a computer hard disk or the like. Thus, there is the need to archive or delete the data. In such instances, however, data useful for performing the analyses is not necessarily available in real time.

Another drawback is the lack of controllability of the MCS 15 as to when the data is obtained and how the data is analyzed. Data which is simply obtained periodically from the MCS 15 does not necessarily have any relationship with respect to "peak" or "off-peak" operation periods of the machine. This can result in misdiagnoses of the machine wear due to a lack of correlation between the data samples and the particular time at which the samples were taken.

In view of the aforementioned shortcomings associated with a MCS, there is a strong need in the art for a computer based system interface for obtaining and analyzing data produced by the MCS. In particular, there is a strong need for a system interface which allows the user to define the intervals at which data is obtained. Moreover, there is a strong need for a system interface which allows the user to define limits for identifying alarm conditions based on the output of the MCS. There also is a strong need for a system interface which is able to process the raw data produced by the MCS in order to reduce the overall amount of data stored, while at the same time not completely losing the integrity of the data.

SUMMARY OF THE INVENTION

According to the present invention, a computer-based system interface is provided which prompts the MCS for data at user defined intervals. Such user defined intervals may be at peak load periods or "off-peak" periods during the operation of a machine. In addition, the system interface parses the data such that raw data produced by the MCS is processed and compressed with predefined algorithms and the processed data is stored in the computer. By processing the data, the user may keep substantial amounts of data pertaining to the history of the machine without the need for deleting or archiving data. The processed data is used in ongoing banding or statistical alarming for evaluating the condition of the machine based on the particle content in its lubricating fluid. Thus, the present invention provides for real-time condition monitoring without forcing the user to either limit the periods the trending is performed or to delete real time data from the storage device due to memory storage limitations.

In accordance with one particular aspect of the invention, a system interface is provided for acquiring data from a microwave conductivity sensor which produces data related to an electrical property of a fluid within a resonant cavity included in the microwave conductivity sensor, the system interface including a memory storing a program; and a computer for executing the program stored in the memory for causing the computer to prompt the microwave conductivity sensor to transmit the data to the computer and to parse the data for particle size information.

According to another aspect of the invention, a memory medium having stored therein a machine readable code is provided, the machine readable code being executable by a computer in order to acquire data from a microwave conductivity sensor which produces data related to an electrical property of a fluid within a resonant cavity included in the microwave conductivity sensor, the computer executing the code stored in the memory medium to cause the computer to prompt the microwave conductivity sensor to transmit the data to the computer and to parse the data for particle size information.

According to still another aspect of the invention, a method for detecting, over predefined intervals, conductive particles of a fluid material within a resonant cavity is provided, including the steps of: producing a frequency excitation signal with a microwave conductivity sensor, the sensor having a microwave driver circuit for producing the signal; introducing the signal into the resonant cavity with a probe; detecting at least one parameter of conductive particles in the resonant cavity with a detector, the detector providing input data to a controller connected to a computer; executing the computer to prompt the microwave conductivity sensor to send data to the computer; and parsing the data into segments relating to the size of the particles.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE PREFERRED EMBODIMENT

The present invention will now be described with reference to the drawings, wherein like reference numerals are used to refer to like elements throughout.

Figure 3:
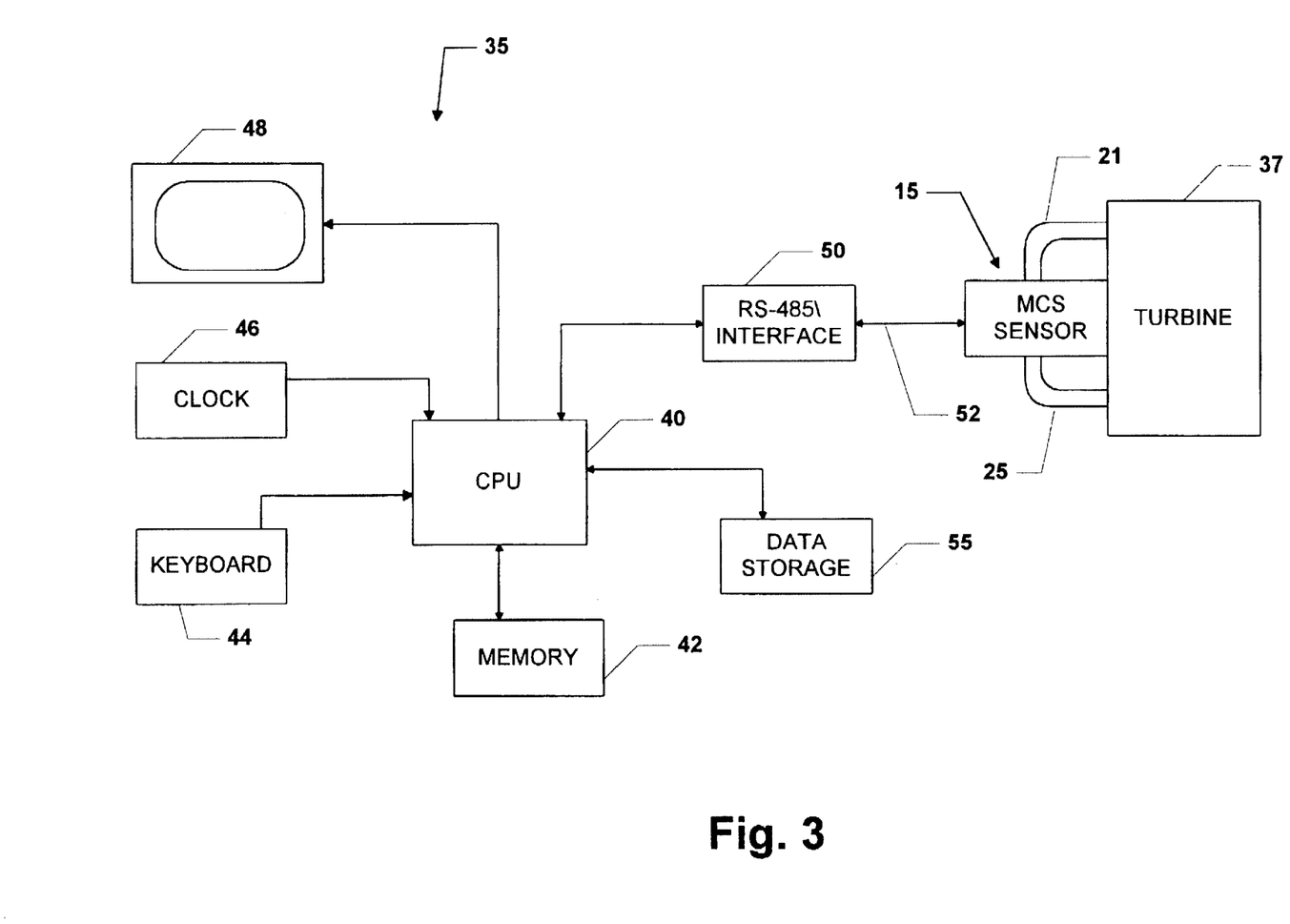
FIG. 3 is a block diagram of a computer based system interface for controlling operation of the MCS and processing the raw data in accordance with the present invention.

Referring initially to FIG. 3, a computer based system interface for operating the MCS 15 is generally designated 35. In the exemplary embodiment, the MCS 15 sits in the lubricant stream of a turbine 37 or other type machine. The MCS 15 receives the lubricating fluid from the turbine 37 via its input pipe 21, and returns the fluid to the turbine 37 by way of its output pipe 25. Preferably, the MCS 15 resides in the return line from a specific bearing group, e.g., an outboard or inboard thrust bearing, etc., or tied into the return line from all components into a main reservoir for the lubricating fluid. In the exemplary embodiment, the MCS 15 is used to evaluate the condition of the machine by performing conductivity measurements of the fluid in real-time. However, it will be appreciated that the present invention can be used in a variety of environments where it is desirable to obtain, store and/or evaluate data from the MCS 15.

The system interface 35 is computer based and is implemented, most preferably, using a personal computer such as a conventional IBM compatible personal computer (IBM PC). The system interface 35 includes a CPU 40 for carrying out the various computing, processing and control operations described herein. The CPU 40 is connected to a system memory 42 which may include both RAM and ROM for storing one or more computer programs which are executed by the CPU 40 in order to carry out the various functions described herein. The CPU 40 can be programmed to perform the various functions using conventional programming techniques. It will be apparent to those having ordinary skill in the art of computer programming in light of the present disclosure how programs can be written in any of a variety of languages such as C, Pascal, etc., without undue effort, to cause the CPU 40 to perform each function. Hence, additional detail is omitted. These programs are stored in the memory 42, preferably on a hard drive or the like, but could also be stored via floppy disk which forms part of the memory 42 by way of a floppy disk drive (not shown).

A keyboard 44 is connected to the CPU 40 for allowing a user to input information such as alarm limits, time intervals or periods during which the MCS 15 is to be prompted for data, etc. A system clock 46 provides the CPU 40 with a time reference enabling the CPU 40 to keep track of the date and time. A display 48 is also connected to the CPU 40 and is used to display information including information based on the data from the MCS 15, alarm conditions, setup menus, etc. The CPU 40 communicates serially with the MCS 15 by way of an RS-485 serial interface 50. Data and control information transmitted between the CPU 40 and the MCS 15 is delivered by way of a serial bus 52. As will be described more fully below, the CPU 40 transmits prompts to the MCS 15 at user defined time periods and/or intervals via the bus 52. The MCS 15 receives the prompts and in response transmits the raw data obtained from the resonant cavity to the CPU 40 via the bus 52 and interface 50. The CPU 40 then processes and stores the raw data in the manner described below and stores the data in a data storage memory 55. Such data storage memory 55 is preferably a hard drive, but could be a floppy disk drive, conventional RAM, etc.

Figure 4:
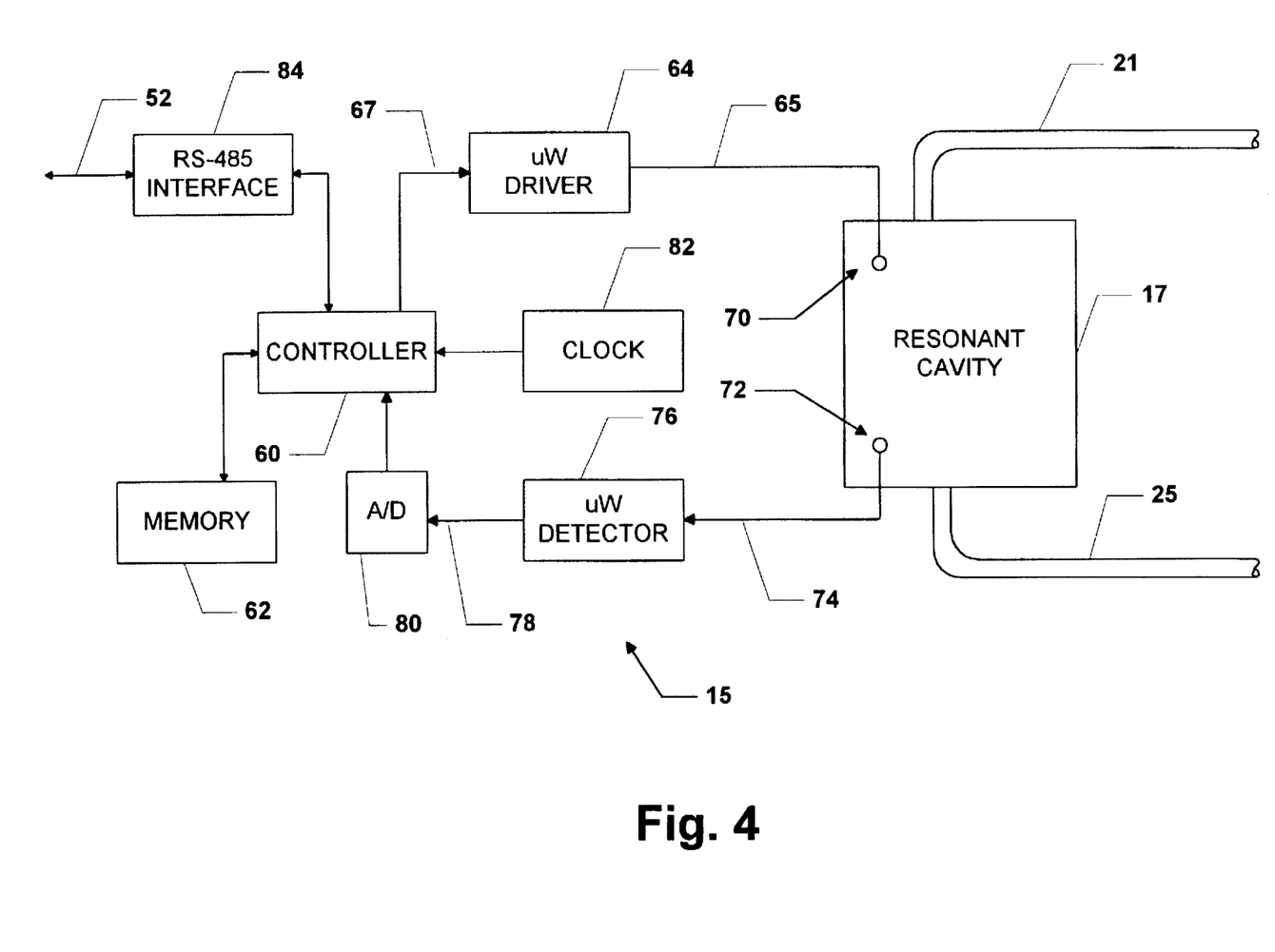
FIG. 4 is a detailed block diagram of the MCS as used in accordance with the present invention.

Referring now to FIG. 4, a detailed block diagram of the MCS 15 is shown. As previously discussed with regard to FIG. 1, the MCS 15 includes a resonant cavity 17 which is filled with fluid from the lubricating stream of the turbine 37 (FIG. 3). In particular, fluid flows through the resonant cavity 17 via the input and output pipes 21 and 25, respectively. The flow rate of the fluid through the resonant cavity 17 is maintained externally (e.g., by way of a pump) such that the resonant cavity 17 remains filled while having a substantially constant flow rate.

The MCS 15 includes a controller 60 which controls all of the operations of the MCS 15 based on program code stored in a system memory 62 attached to the controller 60. In the case of the MCS 15, it also will be apparent to those having ordinary skill in the art of computer programming how to write programs to enable the MCS 15 to carry out its respective operations based on the descriptions provided herein. Thus, additional detail is omitted.

The MCS 15 includes a microwave driver circuit 64 for producing a microwave frequency excitation signal on line 65. The microwave driver circuit 64 can consist of any conventional microwave signal source, and preferably is made up of a signal source whose frequency and phase are controllable by the controller 60 via line 67. The excitation signal on line 65 is introduced into the resonant cavity 17 by way of a probe 70 located in the resonant cavity 17. As mentioned above, the dielectric constant of the fluid within the cavity 17 is dependent upon the size of any conductive particles immersed within the fluid. Consequently, the presence of conductive particles in the resonant cavity 17 will effect the Q factor of the cavity, the amplitude of the resonant waveform in the cavity, and phase of the resonant waveform relative to the excitation signal. In order to detect one or more of these parameters, the MCS 15 also includes a detector probe 72 located inside the resonant cavity 17. The microwave frequency signal detected by the detector probe 72 is provided via line 74 to a microwave detector 76 which can be a crystal, divider circuit, or some other conventional device for providing on line 78 a low frequency analog signal representative of the amplitude and/or phase of the detected signal. The analog signal on line 78 is input to an analog-to-digital (A/D) converter 80 which converts the analog signal into a digital signal using conventional techniques. Thereafter, the digital data is input to and processed by the controller 60 and stored as digital data in the memory 62.

In the exemplary embodiment, the MCS 15 is configured to sample the amplitude and phase of the signal in the resonant cavity 17 every predetermined time period, e.g., every ten seconds. Thus, each data sample $DATA_1$, $DATA_2$, . . . $DATA_n$ stored in the FIFO buffer in memory 62 represents an amplitude and phase of the fluid sample taken at one second intervals. An internal clock 82 connected to the controller 60 provides the appropriate time reference to the controller 60. Assuming, for example, that the FIFO buffer in the memory 62 has a length n=600, the FIFO buffer at any given time will include phase and amplitude data for the past 100 minutes. The data in the FIFO buffer is referred to herein as a string of raw data.

The MCS 15 is connected to the system interface 35 (FIG. 3) via an RS-485 interface 84. In particular, the controller 60 communicates serially with the CPU 40 (FIG. 3) by way of the interface 84 which is connected to the serial bus 52. Upon receiving a control prompt from the CPU 40 via the interface 84, the controller 60 retrieves the phase and amplitude data stored in the FIFO buffer in the memory 62 and communicates it serially to the CPU 40 via the serial bus 52. The 600 data samples covering the last 100 minutes are thereby transmitted to the CPU 40 in time-ordered sequence based on the first in, first out nature of the FIFO buffer. The actual transmission of data and/or control prompts between the system interface 35 and the MCS 15 can be based on virtually any known data transmission protocol. Moreover, although the preferred embodiment of the invention utilizes a serial connection between the system interface 35 and the MCS 15, it will be appreciated that data can also be transmitted in parallel in another embodiment.

The operation of the system interface 35 will now be described with reference to the flow chart presented in FIG. 5. At step 100, the computer program executed by the CPU 40 causes the CPU 40 to prompt the MCS 15 to send to it the raw data via the serial bus 52. More specifically, at user defined intervals and/or times which are input to the CPU 40 via the keyboard 44, the CPU 40 delivers a prompt to the MCS 15 via the serial bus 52. The MCS 15 is programmed to transmit the raw data stored in the memory 62 back to the CPU 40 via the serial bus upon receiving such a prompt. Following step 100, the CPU 40 parses the raw data string according to a parsing algorithm described more fully below in connection with FIG. 8. Generally speaking, the raw data is parsed into segments relating to the presence of large, medium and small size particles in the fluid as detected by the MCS 15. Thus, for example, data amplitude values falling within a first predetermined range are classified as representing large particles. Data amplitude values falling within a second predetermined range are classified as representing medium size particles. Data amplitude values falling within a third predetermined range are classified as representing small size particles. Finally, data amplitude values falling within a fourth predetermined range are classified as representing air bubbles in the resonant cavity. The parsed data with respect to the different sized particles is then evaluated statistically, for example, by comparing the number of particles detected with the mean and standard deviation for the respective sized particles.

The particular ranges for determining particle size can be entered by the user via the keyboard 44. Alternatively, the ranges may be preprogrammed based on known dielectric properties of the fluid being evaluated by the resonance cavity. For each of the data values provided in the raw data from the MCS, the data is compared by the CPU 40 against the predefined ranges and is counted as representing either a large, medium or small size particle, or an air bubble. The totals for each of these ranges, i.e., (number of large)+(number of medium)+(number of small)+(number of air bubbles), for each string of raw data will add up to 600, for example. Of course, total number may be less in case where the data does not fall into any particular range. The CPU 40 then stores these totals in the data storage memory 55 in step 102, as opposed to storing the raw data itself. In this manner, the amount of data which is stored by the system interface 35 is greatly reduced as compared to the case where all of the raw data is stored for subsequent analysis. This avoids the need for archiving the data and/or deleting the data so as to limit the ability to perform subsequent trending analyses. The totals for the large, medium and small sized particles, together with the total of air bubbles detected in the string, are stored by the CPU 40 together with a corresponding date and time stamp indicating the day and time the data was obtained by the MCS.

Figure 5:
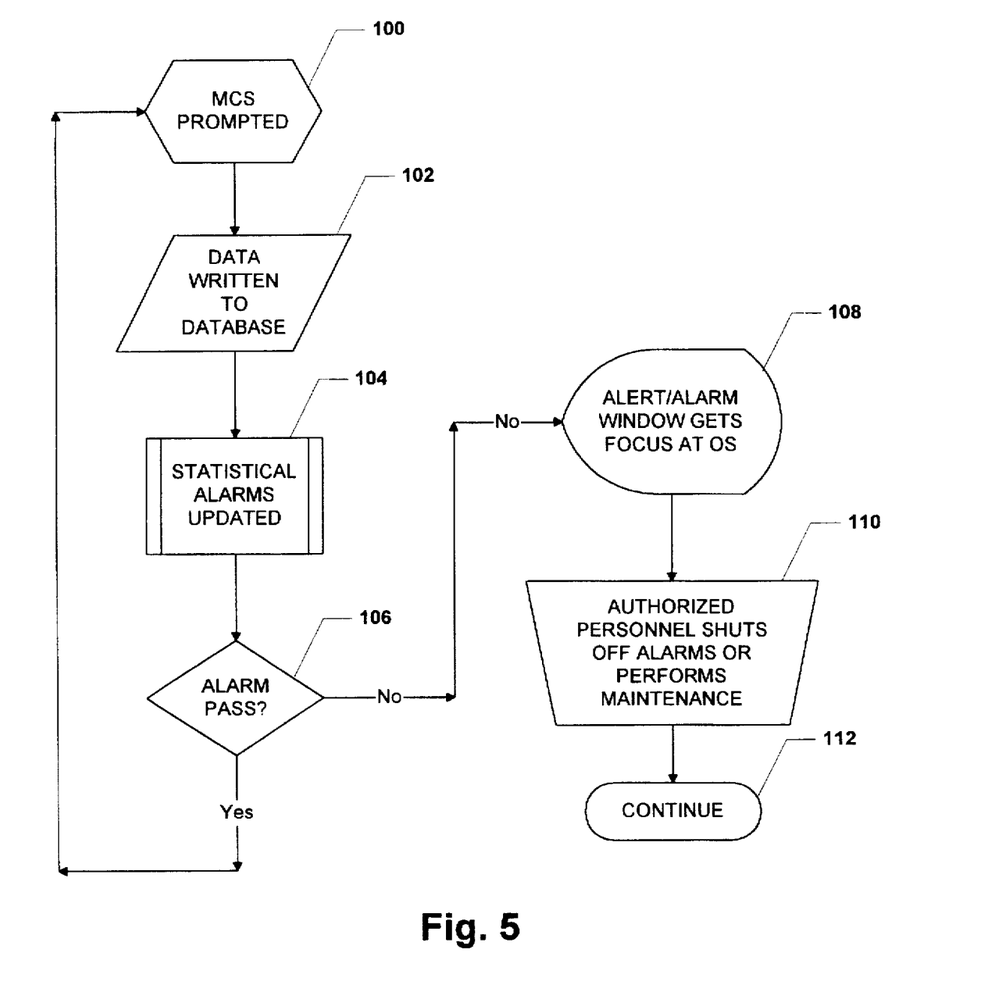
FIG. 5 is a flow chart illustrating the operation sequence of the system interface in accordance with the present invention.

Continuing to refer to FIG. 5, after the totals of the respective sized particles are determined by the CPU 40 in step 102, the system 35 proceeds to step 104 in which the statistical alarms are updated. More specifically, the preferred embodiment of the invention is programmed such that the CPU 40 maintains in memory 42 an ongoing statistical analysis of the number of respective sized particles determined to be present in the fluid based on the MCS 15 data. For example, the CPU 40 may be programmed to keep a running record of the mean and standard deviation with respect to each of the number of large, mid and small sized particles per data string. If the number of respective sized particles in any given data string exceeds the previous mean by more than "X" times the standard deviation, an alarm condition is created as is discussed in more detail below in connection with FIG. 8. The term "X" can be an integer value which is input by the user for each of the ranges, thereby allowing the user to tighten the alarm bands over time by reducing the value of X in each particular range. It is noted that the statistical mean and standard deviation can be computed by the CPU 40 from the compressed totals stored in the data storage memory 55. In addition, statistical values for the respective ranges may be separated further. For example, the CPU 40 can be programmed to receive user defined time periods during which raw data from the MCS 15 is to be obtained and compared with previously obtained data from the same user defined time period from previous days. Thus, for example, the CPU 40 may maintain statistical alarm values for data obtained during "peak" turbine operation, and a separate set of statistical alarm values for data obtained during "off-peak" operation. In such case, the CPU 40 is programmed to be able to receive user defined values of "X" corresponding to the alarm band for each respective type of operation.

Still referring to step 104, the parsed data totals from the current string are used by the CPU 40 to calculate the updated mean and standard deviation for each of the particle size totals and the air bubble total taking into account the newly obtained data. Thereafter, the system interface 35 proceeds to step 106 in which it is evaluated whether the current data string particle totals pass the various statistical alarms, i.e., are within X times the standard deviation for the particular particle size or number of air bubbles. If the current data string does not pass each of the alarms in step 106, the system interface 35 proceeds to step 108 where an alarm message is displayed by the CPU 40 on the display 48. The alarm message preferably indicates which alarm(s) where not successfully passed. In addition, or in the alternative, the CPU 40 causes an alarm to sound via a speaker connected to the CPU 40 (not shown).

In the preferred embodiment, the system interface 35 is based on an IBM-PC compatible computer running the Windows NT operating system. Consequently, the computer can be performing other applications via multitasking while continuing to control and process data from the MCS 15. Thus, the computer is not tied up solely for purposes of the MCS 15 and is available for other applications. Nevertheless, in step 108 the alarm condition detected by the CPU 40 causes the CPU 40 to temporarily seize the operating system, regardless of any other applications which might be running, in order to display a window indicating that an alarm has been triggered. Then, the user in step 110 must shut off the alarm(s) via inputs on the keyboard 44. In addition, or in the alternative, maintenance is performed on the turbine to determine and eliminate the cause for the abnormal amount of particles in the lubricating fluid. According to the preferred embodiment, the CPU 40 is programmed such that the alarm(s) can be shut off by the user via the keyboard 44 only if the user first enters a password indicating that the user is authorized to disable the alarms and/or alter the alarm criteria. The CPU 40 is programmed to prompt the user for such information and to deny access in the absence of receipt of such password. This helps to protect equipment against unintentional (or intentional) misuse by unauthorized employees. Improper shutting off of alarm conditions could result in the turbine staying in an alarm condition without maintenance or engineering staff being aware of the conditions.

Following step 110, the system interface 35 proceeds to step 112 in which the system continues normal operation. Referring back to step 106, in the event the current data string does pass the respective alarms, the system interface 35 returns to step 100 for the next time the CPU 40 prompts the MCS 15 for data.

Figure 6:
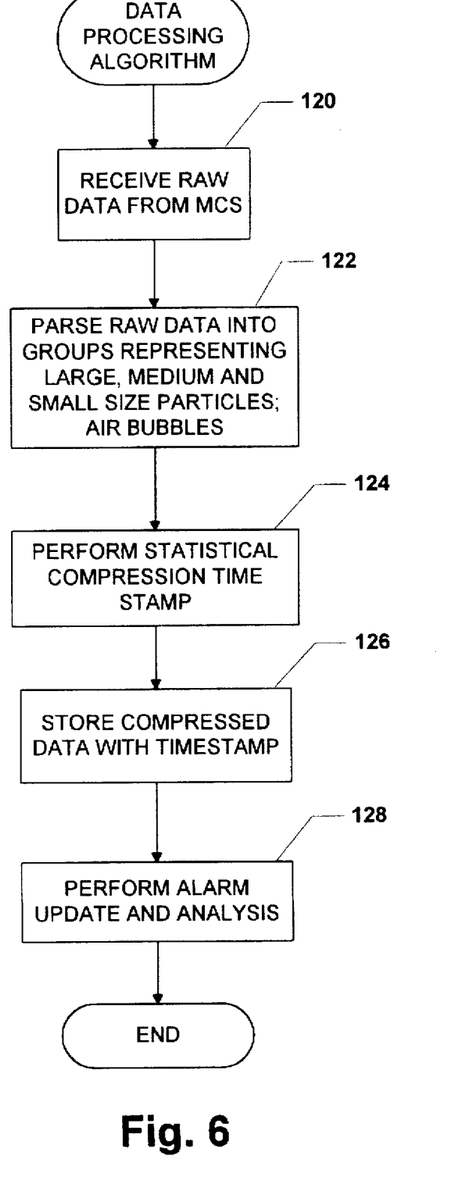
FIG. 6 is a flow chart illustrating how raw data from the MCS is processed in accordance with the present invention.

Referring briefly to FIG. 6, a flow chart is presented which identifies in more detail the above-discussed processing of the string data received from the MCS 15 upon being prompted by the CPU 40. The flow chart of FIG. 6 corresponds primarily to steps 102–106 described in connection with FIG. 5. In step 120, the CPU 40 receives the raw data string from the MCS 15. Next, in step 122 the CPU 40 parses the raw data, which is received in time order, into group totals representing the number of large, medium and small size particles, and the number of air bubbles. In step 124, the CPU 40 performs a statistical compression in the sense that the raw data string is reduced to a series of four totals. The CPU 40 generates a time and date stamp, and in step 126 the CPU 40 stores the compressed data and stamp in the data storage memory 55. Then, as described above, the statistical alarms are updated and the compressed data from the data string is compared against the alarms as represented in step 128.

It will be appreciated that other types of data compression are also possible without departing from the scope of the invention.

Figure 7:
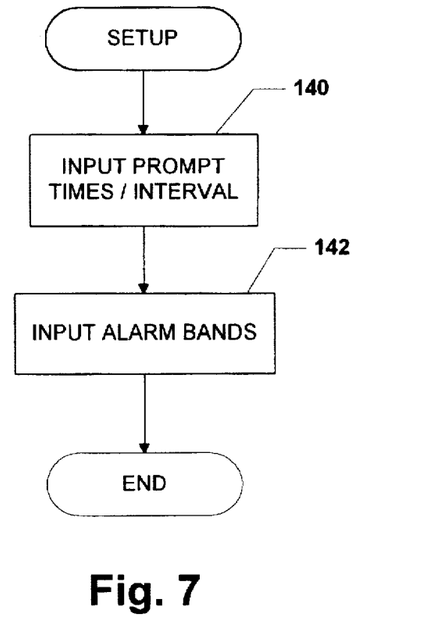
FIG. 7 is a flow chart representing a setup routine performed in accordance with the present invention.

Referring now to FIG. 7, a setup routine which can be followed by the user is shown. In step 140, the user enters the specific times and/or intervals the system interface 35 is to prompt the MCS 15 for raw data. Such information is preferably input by the user via the computer keyboard 44 (FIG. 3) as the information is displayed on the display 48. The CPU 40 is programmed to display appropriate setup windows on the display 48, providing the user with visual prompts as to the information to be entered. In step 142, the CPU 40 is programmed to prompt the user via the display 48 to enter the desired alarm bands, i.e., the value of "X" discussed above in connection with each of the alarm limits. Preferably, the CPU 40 requires that the user enter a password prior to allowing the alarm bands to be set.

Figure 8:
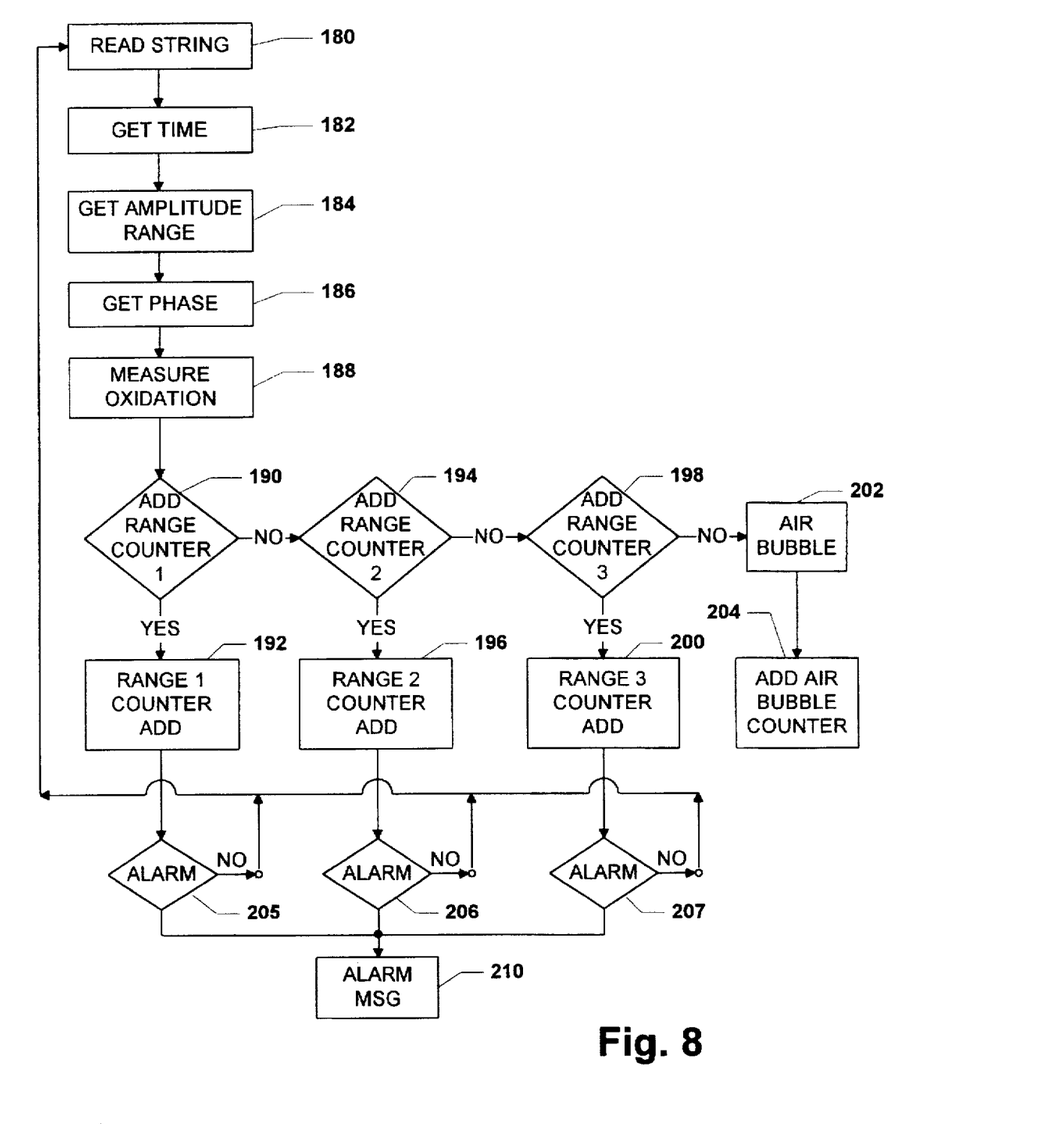
FIG. 8 is a detailed flow chart representing a parsing algorithm for parsing the raw data in accordance with the present invention.

FIG. 8 shows a further detailed flow chart emphasizing an embodiment of the parsing algorithm and alarm evaluation according to the present invention. In this embodiment, the raw data from the MCS 15 is received by the CPU 40 in response to a prompt sent to the MCS 15 according to a user defined time and/or interval as represented in step 180. In step 182, the data received from the MCS 15 is parsed into time order. In the preferred embodiment, the raw data is delivered from the MCS 15 in time ordered sequence so as to perform step 182 automatically. In step 184, the range of the amplitude values for the data string is computed by the CPU 40. Step 184 further parses the data string in order to prepare it for subsequent decisions. Next, in step 186, the phase data which is embedded in each of the samples from the data string is obtained by the CPU 40. Then, in step 188 the oxidation of the fluid is measured from the phase information.

Beginning in step 190 for each of the amplitude values in the string data, it is determined whether the range1 counter, corresponding to large size particles, should be incremented. For example, it can be determined empirically that predefined large size particles in the fluid within the resonant cavity 17 results in amplitude values within the range of $L_l$, to $L_h$. Similarly, it can be determined empirically that predefined medium and small size particles in the fluid within the resonant cavity 17 result in amplitude values within the ranges of $M_l$ to $M_h$, and $S_l$ to $S_h$, respectively. Thus, in step 190, it is determined if the particular amplitude value for the current data sample in the string is within the range of $L_l$ to $L_h$. If yes, the range1 counter is incremented by 1 in step 192. If not, the amplitude value is compared to the range $M_l$ to $M_h$ in step 194 corresponding to a medium size particle. If the amplitude value does fall within the range $M_l$ to $M_h$, the range2 counter is incremented in step 196. If not, the amplitude value is compared to the range $S_l$ to $S_h$ in step 198 corresponding to a small size particle. If the amplitude value does fall within the range $S_l$ to $S_h$, the range3 counter is incremented in step 200. If not, the CPU 40 proceeds from step 198 to step 202 in which it is concluded that an air bubble exists in the resonant cavity 17 for that particular data sample. As a result, an air bubble counter is incremented in step 204.

It will be appreciated that the range1 through range3 counters together with the air bubble counter are reset to zero before each prompting of the MCS 15 for a new raw data string. After steps 190–204 have been carried out with respect to each of the data samples in the current string, the totals in the respective counters serve as the above-mentioned statistically compressed data values which are stored in the data storage memory 55 together with a time stamp as discussed above. The aforementioned statistical alarms are then updated as discussed above. Thereafter, the outputs of each of the range1 through range3 counters represented in steps 192, 196 and 200, respectively, represent the totals of the large, medium and small particles. These totals are then compared in steps 205–207, respectively, against the standard mean plus X times the standard deviation with respect to each particular size of particle as discussed above. If an alarm is passed successfully, the system returns to step 180. However, if an alarm is not satisfied, the system proceeds to step 210 whereat the alarm is indicated as explained above.

In view of the above description, it will be appreciated that the system interface 35 of the present invention provides a manner for obtaining, processing and evaluating data from an MCS without the need to archive and/or delete data. The present invention allows data to be retained and evaluated for purposes of detecting wear based on the presence of conductive particles in a fluid. The time and data stamping of the data according to load time and performance enables the user to achieve more useful information as compared to the raw data produced by the MCS. For example, power generation turbines experience different load conditions throughout the course of the day. Conventional programs fall short due to the sampling of data during various load periods can lead to false results, either falsely optimistic or pessimistic. For example, trending wear and oxidation levels across light load periods may lead to false normal readings.

Regarding the alarms according to the present invention, standard mean plus (integer) times standard deviation is used although the integer is editable by the user. The user is therefore able to tighten the alarm bands over time. Other on-line condition monitoring systems fall short since slow increases in wear or oxidation can go undetected.

As for the aforementioned password usage for setting, altering, and/or shutting of the alarm conditions, such passwords offer increased protection against misuse. An alarm may be shut off, application aborted, statistics edited, or database entries deleted dependent upon protection levels set by a system administrator via one or more levels of passwords. In addition to requiring passwords, the CPU 40 is programmed to keep an electronic log referencing what changes were made to the system setting, who made the changes, and when they were made. Expiration dates are included with the passwords such that passwords are required to be renewed to help protect against misusage.

Another aspect of the invention relates to the use of the RS-485 interface for connecting the system interface 35 to the MCS 15. The RS-485 interface does not have the impedance limitations associated normally associated with cable length. This allows full duplex communication across on the order of 4500 feet of inexpensive twisted pair cable which is shielded and can be run along a noisy plant floor (a typical environment for the MCS).

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A system interface for acquiring data from a microwave conductivity sensor which produces data over time related to an electrical property of a fluid within a resonant cavity included in the microwave conductivity sensor, the fluid used in operation of a machine, the system interface comprising:

a memory storing a program; and a computer for executing the program stored in the memory for causing the computer to prompt the microwave conductivity sensor to transmit the data to the computer and to parse the data for particle size information, and for analyzing the particle size information based on a predefined criteria to ascertain information relating to an operational condition of the machine.

2. The system interface of claim 1, wherein the computer stores the particle size information in a data storage memory in lieu of storing the data received from the microwave conductivity sensor.

3. The system interface of claim 1, wherein the microwave conductivity sensor transmits the data to the computer via serial communications.

4. The system interface of claim 1, wherein the computer comprises a personal computer.

5. The system interface of claim 1, wherein data based on the data received from the microwave conductivity sensor is stored by the computer together with a time or date stamp.

6. The system interface of claim 1, wherein the computer calculates dynamic alarms for evaluating the particle size information.

7. The system interface of claim 6, wherein a parameter of the dynamic alarm can be altered by a user after a password has been entered.

8. The system interface of claim 1, wherein the microwave conductivity sensor is connected to the computer by way of a RS-485 interface.

9. A memory medium having stored therein a machine readable code, the machine readable code being executable by a computer in order to acquire data from a microwave conductivity sensor which produces data over time related to an electrical property of a fluid within a resonant cavity included in the microwave conductivity sensor, the fluid used in operation of a machine, the computer executing the code stored in the memory medium to cause the computer to prompt the microwave conductivity sensor to transmit the data to the computer and to parse the data for particle size information, and further to analyze the particle size information based on a predefined criteria to ascertain information relating to an operational condition of the machine.

10. A method for detecting, over predefined intervals, conductive particles of a fluid material within a resonant cavity, the fluid used in operation of a machine, the method comprising the steps of:

producing a frequency excitation signal with a microwave conductivity sensor, the sensor having a microwave driver circuit for producing the signal;

introducing the signal into the resonant cavity with a probe;

detecting at lease one parameter of conductive particles in the resonant cavity with a detector, the detector providing input data to a controller connected to a computer;

executing the computer to prompt the microwave conductivity sensor to send data to the computer; and parsing the data into segments of data relating to the size of the particles, and analyzing the segments of data based on a predefined criteria to ascertain information relating to an operational condition of the machine.

11. The method of claim 10, wherein the microwave driver circuit comprises a signal source, the frequency and phase of the signal source being controllable by the controller.

12. The method of claim 10, wherein the computer stores the segments of data relating to the size of the particles in a data storage memory in lieu of storing the data received from the microwave conductivity sensor.

13. The method of claim 10, wherein the microwave conductivity sensor transmits the data to the computer via serial communications.

14. The method of claim 10, wherein the prompt is sent to the microwave conductivity sensor according to a user defined time and/or interval.

15. The method of claim 10, wherein the data is delivered from the microwave conductivity sensor in time ordered sequence.

16. The method of claim 10, wherein the range of the amplitude values for the segments of data relating to the size of the particles is computed by the computer.

17. The method of claim 10, wherein phase data which is embedded in the segments of data relating to the size of the particles is obtained by the computer.

18. The method of claim 17, wherein the oxidation of the fluid material is measured from the phase data.

19. The method of claim 10, wherein the computer calculates dynamic alarms for evaluating the segments of data relating to the size of the particles.

20. The method of claim 19, wherein a parameter of the dynamic alarm can be altered by a user after a password has been entered.

* * * * *